United States Patent [19]

Manabe et al.

[11] Patent Number: 4,971,913

[45] Date of Patent: Nov. 20, 1990

[54] METHOD FOR CONTROLLING REAGENT DELIVERY SYSTEM IN AUTOMATIC CHEMICAL ANALYZER

[75] Inventors: Sugio Manabe; Tauneaki Kadogaki, both of Tokyo, Japan

[73] Assignee: Olympus Optical Co., Ltd., Japan

[21] Appl. No.: 139,082

[22] Filed: Dec. 23, 1987

Related U.S. Application Data

[63] Continuation of Ser. No. 614,247, May 25, 1984, abandoned, which is a continuation of Ser. No. 294,618, Aug. 20, 1981, abandoned.

[30] Foreign Application Priority Data

Aug. 22, 1980 [JP] Japan .............................. 55-114644
Aug. 22, 1980 [JP] Japan .............................. 55-114645
Aug. 22, 1980 [JP] Japan .............................. 55-114646

[51] Int. Cl.$^5$ ................... C12M 1/36; G01N 35/00; G01N 35/02
[52] U.S. Cl. ................................. 436/55; 422/62; 422/63; 422/67; 422/68.1; 435/5; 435/289; 436/49; 436/50
[58] Field of Search ................... 435/3, 11, 16, 19, 26, 435/289, 291, 5; 436/47, 49, 50, 55; 364/497, 499; 422/62, 63, 67, 68

[56] References Cited

U.S. PATENT DOCUMENTS

| | | | |
|---|---|---|---|
| 3,912,456 | 10/1975 | Young | 436/47 |
| 4,000,976 | 1/1977 | Kramer et al. | 422/67 X |
| 4,128,628 | 12/1978 | Brooker et al. | 435/289 X |
| 4,169,125 | 9/1979 | Rodriguez et al. | 422/67 X |
| 4,264,327 | 4/1981 | Blum | 435/291 X |
| 4,276,051 | 6/1981 | Ginsberg et al. | 436/47 |
| 4,276,258 | 6/1981 | Ginsberg et al. | 422/67 X |
| 4,338,279 | 7/1982 | Orimo et al. | 422/67 X |

Primary Examiner—Robert J. Warden
Assistant Examiner—Kimberly A. Trautman
Attorney, Agent, or Firm—Arnold, White & Durkee

[57] ABSTRACT

A multi-item automatic chemical analyzer comprising a reagent delivery system for delivering a plurality of reagents of different kinds into reaction vessels in succession is disclosed. The influence of contamination between the reagents upon measurement is reduced or eliminated by controlling the reagent delivery system with a control system comprising a memory unit for storing information representing a relation of the test items, particularly the influence of contamination between the reagents upon the measurement, and a center process unit for controlling the operation of reagent delivery system in accordance with the stored information.

3 Claims, 3 Drawing Sheets

FIG_3
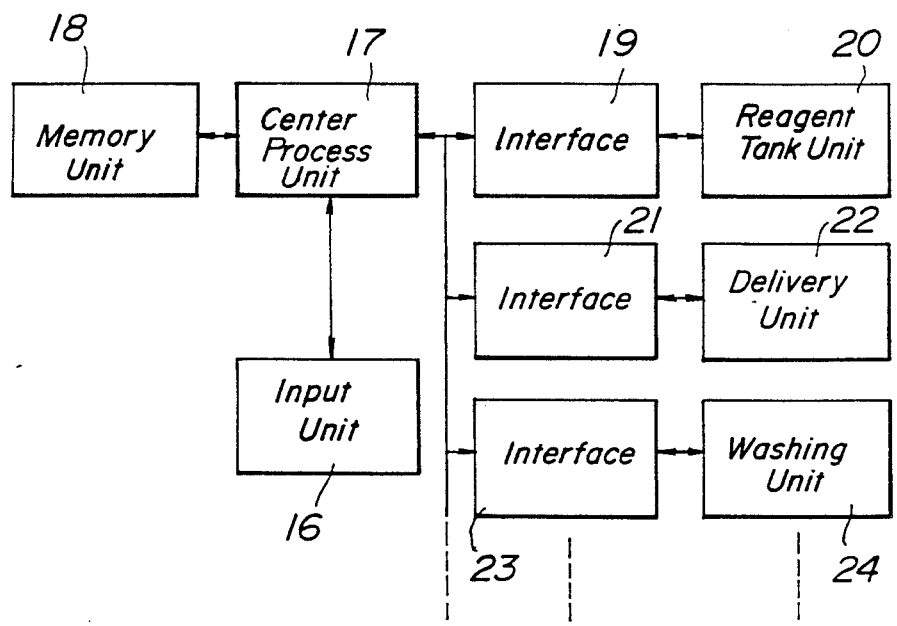
FIG_4
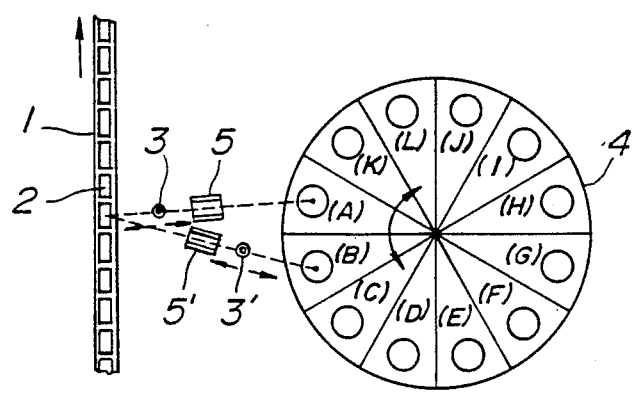

METHOD FOR CONTROLLING REAGENT DELIVERY SYSTEM IN AUTOMATIC CHEMICAL ANALYZER

This is a continuation of application Ser. No. 614,247, filed May 25, 1984, now abandoned, which in turn a continuation of application Ser. No. 294,618, filed Aug. 20, 1981, now abandoned.

BACKGROUND OF THE INVENTION

The present invention relates to a method for controlling a reagent delivery system in an automatic chemical analyzer for automatically analyzing various components in a number of samples such as bloods and urines. Nowadays, various automatic chemical analyzers have been installed in test sections in many hospitals and laboratories and a great amount of accurate analyzing results have been obtained in a speedy manner. Particularly, multi-item automatic chemical analyzers which can measure a number of test items, for example, thirty test items, have been developed and practically used. In known multi-item automatic chemical analyzers, a given reagent to be used for a revelant test item is selected from among a number of necessary reagents for testing a number of test items and a given amount of the selected reagent is delivered by a specialized delivery device in order to avoid possible contamination between reagents of different kinds. That is to say, since each of different reagents are processed by respective delivery devices, there occurs no contamination between the different reagents. However, in such a reagent delivery system, the number of the delivery devices has to be equal to that of the reagents of different kinds. For instance, when thirty different kinds of reagents are to be used in the analyzer, the analyzer should include thirty delivery devices which are operable independently from each other. This results in a large analyzing apparatus that is complicated in construction and expensive in cost. A reagent delivery system in which only those portions which are made in contact with the reagents are provided by the same number as that of the different reagents and any one of them is selectively coupled with a main body of the reagent delivery device has also been proposed. For instance, there are provided a number of probes or nozzles which are selectively connected to a syringe by means of a switching valve. However, in such a system, since the probes must be changed at a middle of a liquid path, liquid leakage is liable to occur and thus, the accuracy of reagent delivery might be decreased. Moreover, the larger number of different kinds of required reagents, the more complicated the construction of the reagent delivery system becomes. Another proposal was to deliver all of the different kinds of reagents by means of a single delivery device. However, in such a system, in order to avoid or decrease the contamination between the different reagents, the delivery device must be washed in a special manner. Thus, it is necessary to provide a special washing device of high efficiency which requires a large amount of a washing liquid and thus, it is also necessary to prepare or stock a large amount of the washing liquid. This results in that the analyzer is liable to be large in size.

SUMMARY OF THE INVENTION

The present invention has for its object to provide a novel and useful method for controlling an automatic chemical analyzer of multi-item type, in which the number of delivery units can be made smaller than that of required reagents of different kinds and the amount of reagents to be delivered can be accurately controlled without causing serious contamination between different reagents even if an amount of a washing liquid is decreased to a minimum value.

It is an object of the present invention to provide a method of controlling a reagent delivery system for delivering a plurality of different reagents into successive sample-containing reaction vessels in an automatic chemical analyzer for measurement of corresponding test specimens in a plurality of test items, comprising the steps of:

preparing at least one reagent delivery device, the number of which is smaller than that of the reagents of different kinds;

storing in memory means information representing a predetermined relation between the test items with respect to the influence of contamination between the reagents upon a measurement; and controlling the operation of said reagent delivery device in accordance with said predetermined relation stored in the memory means in such a manner that the measurement is not affected by the contamination between the reagents.

BRIEF DESCRIPTION OF THE DRAWINGS

FIGS. 2 and 3 are block diagrams showing two embodiments of a control system for carrying out the control method of the invention;

FIG. 4 is a schematic plan view illustrating a main portion of another embodiment of the automatic chemical analyzer to which the present invention is applied.

DESCRIPTION OF THE PREFERRED EMBODIMENTS

Figure 1:
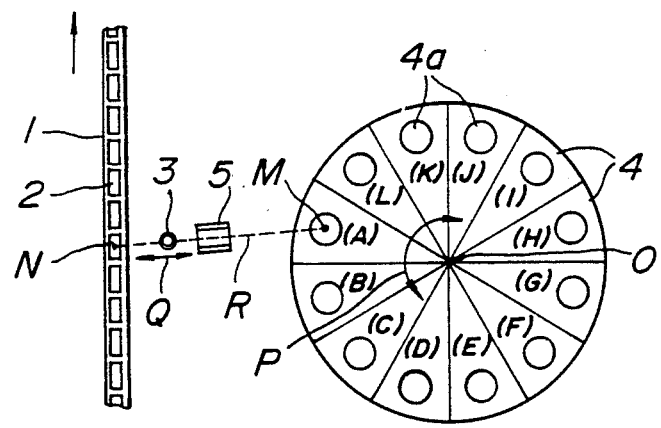
FIG. 1 is a schematic plan view showing a main portion of an automatic chemical analyzer to which the control method according to the present invention can be advantageously applied.

FIG. 1 is a schematic plan view illustrating a main part, particularly a reagent delivery system of an automatic chemical analyzer to which the control method according to the invention can be advantageously applied.

In FIG. 1, reference numeral 1 denotes a reaction line along which a number of reaction vessels 2 are fed intermittently at a given pitch, each reaction vessel containing the respective samples to be analyzed. In the reaction line 1 there is provided a reagent delivery position N at which a predetermined amount of a given reagent is delivered into a reaction vessel 2 by means of a reagent delivery system. The system comprises a nozzle 3 connected to a syringe (not shown). A number of reagents of different kinds (A) to (L) are contained in respective reagent tanks 4 which are rotatably arranged about an axis O as shown by an arrow P. Each of the reagent tanks 4 have openings 4a and any of the openings 4a can be positioned at the reagent aspirating position M by means of a suitable driving and indexing mechanism (not shown). The nozzle 3 of the reagent delivery system can be reciprocally moved between the positions N and M as shown by a double headed arrow Q along a path denoted by a broken line R. At the middle of this reciprocal travelling path R is arranged a washer 5 for cleaning the nozzle 3 with the aid of a suitable washing liquid.

Now the operation of the reagent delivery will be explained. A reagent tank 4 containing a given reagent to be added to a sample in a relevant reaction vessel 2 to conduct a test of a given item, is indexed at the reagent aspirating position M. Then the nozzle 3 is dipped into the reagent to aspirate a predetermined amount of the relevant reagent. Next, the nozzle 3 is moved into the reagent delivering position N on the reaction line 1 and the aspirated reagent is dispensed into the relevant reaction vessel 2 positioned at N. After that the reaction vessel 2 is advanced along reaction line 1, while the given reaction is proceeding. At last the reaction vessel 2 arrives at a photometering position (not shown) and the given component in the liquid contained in the reaction vessel 2 is tested. After dispensing the reagent, the nozzle 3 is fed into the washer 5 and is washed thereby. Then the nozzle 3 is again fed into the aspirating position M and is prepared for aspirating a next reagent which may or may not be the same reagent as that previously aspirated. In the present embodiment, the single nozzle 3 is commonly used for delivering a plurality of reagents of different kinds, in the instant example, twelve kinds of reagents (A) to (L) may be delivered. Therefore, if special measures are not taken, contamination between the different reagents might affect the analysis or tests, and accurate measurement results could not be obtained. The present invention is based on recognition of the fact that the degree of the influence of contamination between the reagents upon the tests and measurement results differs with respective reagents and in some test items, slight contamination does not significantly affect the tests. Of course, in some test items, even the slightest contamination between reagents has a serious influence upon the measurement. For instance, the contamination between the following reagents affects the measurement greatly.

(1) Transaminases such as Glumatate Oxalacetate Transaminases (GOT) and Glumatate Pyruvate Transaminase (GPT) in Karmen method; and dehydrogenases such as Lactic Dehydrogenase (LDH) and α-Hydroxybutyrate Dehydrogenase (α-HBD).

(2) Phosphoric acid buffer solution for use in test items such as Blood Urea Nitrogen (BUN) and Glucose (GLU); and phosphorus.

(3) Reducing agents contained in reagents for measuring iron; and 4-amino-antipyrine (4-A-A) for use in chromatic enzyme test items such as Triglycerides (TG), Glucose (GLU) and Total-cholesterol (T-CHOL).

In the known analyzer, in order to eliminate or decrease the influence upon the measurement due to contamination between reagents, the nozzle of the delivery unit is washed in a special manner with the aid of a great amount of a washing liquid. In the known apparatus, the degree of influence of contamination between reagents has not been taken into account and thus, even if contamination between some reagents does not influence the measurement, the nozzle is washed sufficiently with a large amount of a washing liquid. Therefore, a great amount of washing liquid is wasted and the washing time occupies a substantial part of the analyzing time, so that the efficiency of the analyzer is limited by the time required for washing the nozzle.

According to the present invention, the reagent delivery system is so controlled that the required amount of the washing liquid can be made as small as possible, while the measurement can be protected against the influence of contamination between reagents. In the present invention, information representing a predetermined relation between the test items with respect to the influence of contamination between the reagents upon the measurement is previously established and stored in a memory. The reagent delivery operation is controlled in accordance with said predetermined relation in such a manner that the measurement is not affected by contamination between the reagents. Such control may be carried out in various ways which may be roughly classified into the following three methods.

(1) The order of items to be tested successively is controlled by means of a computer.

(2) The operation of the washing device is controlled by a computer.

(3) A plurality of reagent delivery devices are provided and any one of them is selectively used.

First Control Method

Figure 2:
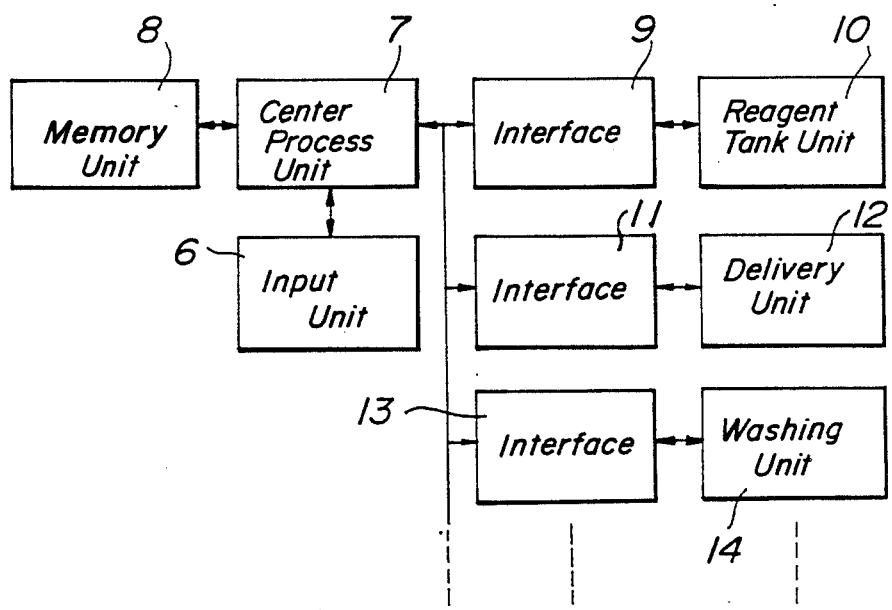

FIG. 2 is a circuit diagram showing an embodiment of a control system for controlling the reagent delivery system in accordance with the above mentioned first method. The control system comprises an input unit 6 having a key board, a floppy device, etc. for introducing or entering information for denoting one or more test items to be measured for respective samples. This information of the test items is supplied through a center process unit 7 to a memory unit 8 and is stored in the memory unit 8. The memory unit has also stored a predetermined relation between the test items with respect to the influence of contamination between the reagents. In the first control method, the above relation represents combinations of test items using reagents the contamination of which greatly affects the measurement. The center process unit 7 controls the operations of a reagent tank unit 10, a delivery unit 12 and a washing unit 14 by means of respective interfaces 9, 11 and 13. The unit 7 determines the order of effecting the required test items in such a manner that test items which might cause a problem due to contamination of reagents could not be measured in succession.

An example of determining the measuring order will be explained hereinbelow. In this example, items (A) to (L) can be tested by the analyzer and have a mutual relation with respect to contamination between reagents as shown in the following table.

| | A | B | C | D | E | F | G | H | I | J | K | L |
|---|---|---|---|---|---|---|---|---|---|---|---|---|
| L | | | | | | | | | | | | |
| K | | | | | | | | | | | | |
| J | | | | | | | | | | | | |
| I | | | | | x | | | | | | | |
| H | | | | | x | | | | | | | |
| G | | | | | | | | | | | | |
| F | | | | | | | | | | | | |
| E | | | | | | | | | | | | |
| D | x | x | | | | | | | | | | |
| C | x | x | | | | | | | | | | |
| B | | | | | | | | | | | | |
| A | | | | | | | | | | | | |

In the table, a mark x denotes test items in which contamination of reagents has a large influence upon the measurement. For instance, if a reagent for use in a test item E is mixed with a reagent for use in a test item I or H, the measurement of the test item I or H might be greatly influenced by the contamination of these reagents. It is apparent from the above table that reagents for use in test items F, G, J, K and L do not have any influence upon the measurement even if these reagents are mixed with reagents for use in any other test items.

Now it is assumed that five samples Nos. 1 to 5 are to be analyzed with respect to the following test items.

No. 1: A, B, C, E, F, H
No. 2: A, B, D, J
No. 3: A, B, C, D, E, H, J, K
No. 4: E, F, H, I, L
No. 5: A, B, C, D, E, F

These test items are introduced by the input unit 6 and are stored in the memory unit 8 under the control of the center process unit 7.

It is apparent that if the measurement is carried out in the order mentioned above, it is influenced by the contamination of reagents. For instance, the test item B for the second sample No. 2 could not be directly followed by the test item D for the same sample. According to the invention, the order of measurement is converted into the following order by taking into account the influence of contamination between the reagents.

No. 1: A, B, E, C, F, H
No. 2: A, B, J, D
No. 3: E, A, B, H, C, D, J, K
No. 4: E, F, H, I, L
No. 5: A, B, E, C, D, F

According to the invention, the order of test items to be analyzed successively is changed such that test items using reagents which might produce the problem of contamination are not analyzed successively as far as possible. Therefore, contaminating reagents are delivered successively through the reagent delivery device a minimum number of times.

In the worst case, test items having large influence of contamination might be made successive, although such a case is very rare. In such a case, the influence of contamination may be eliminated by taking any one of the following steps.

(1) A test item which has no influence of contamination is intentionally introduced, even if this test item is not required to be measured.
(2) The delivery of reagent is stopped for one cycle and a washing operation is effected in this cycle.
(3) A calibration using a reagent which hardly affects the succeeding test item is carried out.

Second Control Method

In the second control method according to the invention, the washing operation in the reagent delivery system is so controlled that only when a test item using a reagent which affects a test item to be measured next has been effected, the nozzle of the reagent delivery device is washed sufficiently with a large amount of a washing liquid. For this purpose, a washing unit is controlled by a computer in accordance with the predetermined relation among the test items.

FIG. 3 is a circuit diagram showing an embodiment of a control system for controlling the reagent delivery system in accordance with the above mentioned second control method. The control system comprises an input unit 16 having a key board, a floppy device, etc. for introducing or setting information for denoting one or more samples to be measured for respective test items. This information of the test items is supplied through a center process unit 17 to a memory unit 18 and is stored therein. In the memory unit 18 there is also stored an information representing combinations of the test items using reagents the contamination of which greatly affects the measurement. The center process unit 17 controls the operations of a reagent tank unit 20, a delivery unit 22 and a washing unit 24 via respective interfaces 19, 21 and 23. In the second control method, the washing unit 24 for washing the nozzle 3 (FIG. 1) of the reagent delivery device is controlled in a special manner in accordance with the information representing the predetermined relation of the test items. In this embodiment, all the test items are classified into two groups, i.e. a first normal group in which the contamination of reagents does not affect the measurement and a second abnormal group in which the contamination of reagents has serious influence upon the measurement. The center process unit 17 judges which group the relevant test item belongs to.

If the items belonging to the abnormal group are to be measured successively, the degree of washing in the washing unit 14 is increased. This may be carried out by increasing the amount of the washing liquid.

The degree of the washing may also be enhanced by following measures instead of increasing the amount of the washing liquid.

(1) The washing time is prolonged. This includes increasing the number of washing operations.
(2) A plurality of washing mechanisms are provided and in usual washing, only one mechanism is used, but in the enhanced washing, a plurality of washing mechanisms are operated. It should be noted that this control may be effected also by selectively operating a plurality of parts provided in a single washing mechanism.
(3) In case of providing a syringe in a washing pump, stroke of a syringe piston is varied so as to change an amount of the washing liquid dispensed from the syringe as well as the pressure of the washing liquid stream.

Third Control Method

In the third control method, a number of reagents to be used are classified into the plurality of groups, and in each group the contamination of reagents does not completely or substantially affect the measurement. In case of delivering the reagents in the same group, use is made of a single and common delivery device. In the above example, GOT, GPT, one or more test items using phosphoric acid buffer solution, and iron component are classified into a first group, and LDH, α-HBD, phosphorus, TG and T-CHOL are classified into a second group. The reagents in each group are delivered by means of respective delivery devices. In such a case it is sufficient to provide only two delivery devices.

FIG. 4 is a schematic plan view showing an embodiment of the analyzer which is controlled by the third control method. In this embodiment, similar portions to those illustrated in FIG. 1 are denoted by the same reference numerals as those used in FIG. 1. This analyzer is different from the previous embodiment shown in FIG. 1 only in that a second delivery device comprising a second nozzle 3' and a second washing unit 5' is provided and this second delivery device can be operated independently of the first delivery device comprising a first nozzle 3 and a first washing unit 5. A reagent tank unit comprising a plurality of reagent tanks 4 containing the reagents of different kinds is commonly used for the first and second reagent delivery devices.

Figure 5:
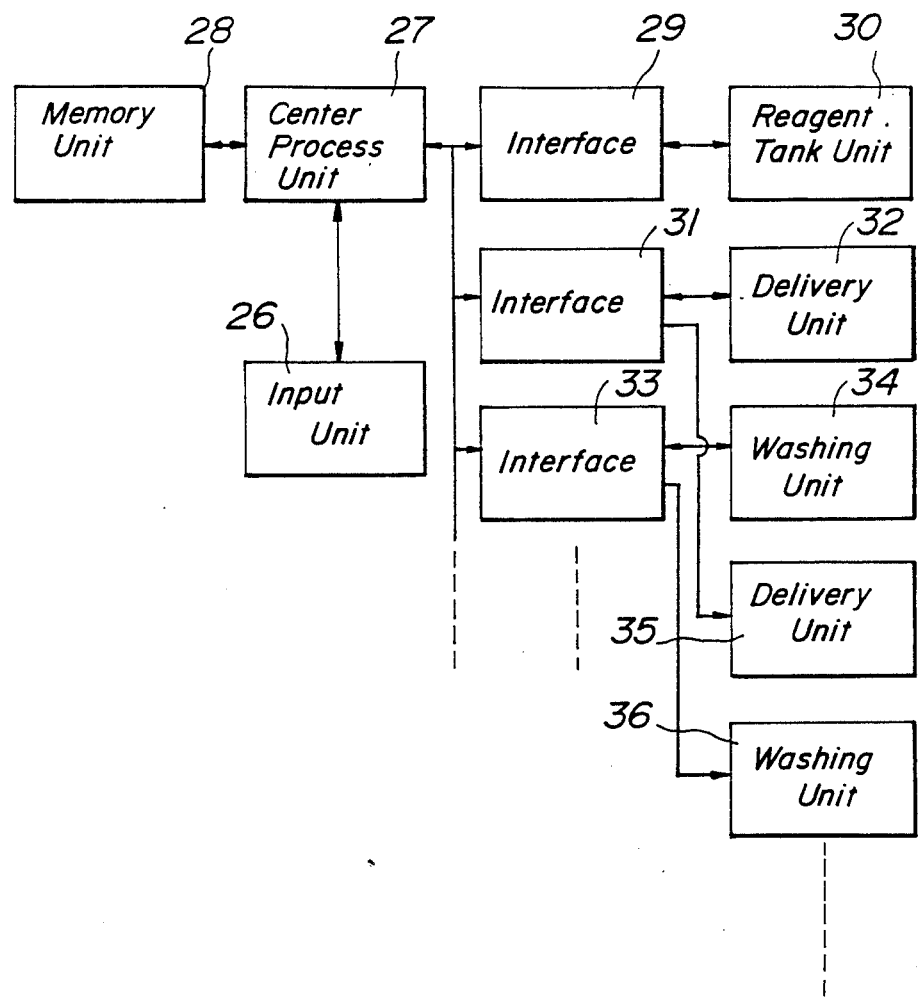
FIG. 5 is a block diagram of the control system for controlling a delivery system in accordance with the method of the present invention.

FIG. 5 is a block diagram depicting one embodiment of the control system in accordance with the third control method. The control system of this embodiment comprises an input unit 26 including a key board, a floppy device, etc. for entering information about test items to be analyzed for respective samples. This information is supplied through a center process unit 27 to a memory unit 28 and is stored therein. Also stored in the memory unit 28 is information about a plurality of groups into which the test items have been previously classified in accordance with the above explained criterion. The center process unit 27 controls operations of a reagent tank unit 30, a plurality of delivery units 32 and 35 and a plurality of washing units 34 and 36 by means of respective interfaces 29, 31 and 33 in accordance with a predetermined program. The first delivery unit 32 and washing unit 34 are selectively used for delivering a given amount of any reagent belonging to said first group. Similarly, the second delivery unit 35 and washing unit 36 are exclusively used for delivering the reagents classified in the second group. Upon effecting particular test items, the center process unit 27 judges which group the relevant test item belongs to on the basis of the information stored in the memory unit 28 to selectively operate either one of the two reagent delivery devices 32, 34 and 35, 36.

As explained above in detail, in the reagent delivery control method according to the present invention, the following advantages can be effectively obtained.

(1) Since the number of the reagent delivery devices can be made sufficiently smaller than that of the reagents of different kinds, the whole analyzer can be made small in size.

(2) The reagent delivery device can be simply constructed and the accuracy of the reagent delivery can be made high.

(3) The influence of the contamination between the reagents upon measurement can be reduced or eliminated without using a great amount of the washing liquid.

(4) Since the amount of the washing liquid can be made smaller, the tank containing the washing liquid can be a small one.

(5) Since the time required for washing can be minimized, the efficiency of the analyzer can be increased, so that many more samples can be processed per unit time.

(6) The control of the reagent delivery can be effected by the computer in a simple manner and thus, the cost of the analyzer is not made high.

The present invention is not limited to the embodiments mentioned above, but many modifications could be conceived by those skilled in the art within the scope of the invention. For instance, the number of the reagent delivery devices is not limited to one or two, but more than three reagent delivery devices may be provided by taking into account the influence of contamination between the different kinds of reagents. In such a case, the efficiency of the washing devices of these reagent delivery devices may be made different from one another. In a case where a test item requires a plurality of reagents, use may be made of a reagent delivery device of a multi-step or multi-shot type. Further, in the above embodiments, the three control methods are separately used, but it is a matter of course that two or three methods may be combined in various manners.

What is claimed is:

1. A method of controlling a reagent delivery system for delivering a plurality of different reagents into successive sample-containing reaction vessels in an automatic chemical analyzer for measurement of test specimens in a plurality of corresponding test items, comprising the steps of:

providing a reagent delivery device for delivering a plurality of different reagents corresponding to respective test items;

storing in memory means information representing a predetermined relationship between the test items with respect to the influence of contamination between said different reagents upon a measurement of said test specimens;

entering said information by entering means test items to be tested as successive samples;

storing in the memory means the entered test items to be tested as successive samples;

determining a minimum contamination test order for said entered test items in accordance with said stored information to minimize a number of occurrences of analytical measurement contamination between reagents of successive test items in said minimum contamination test order, and controlling the operation of said reagent delivery device according to said minimum contamination test order whereby reagents, are successively delivered a minimum number of times by said reagent delivery device, and whereby no washing of said reagent delivery device is performed between successive delivery of reagents, contamination between which does not affect measurement.

2. The method according to claim 1, further comprising the step of introducing an additional test item into said minimum contamination test order between entered test items using reagents, contamination said additional test item not being one of said entered test items, said additional test item having a corresponding reagent which does not contaminate a reagent corresponding to a succeeding test item in said minimum contamination test order and wherein succeeding tests are performed in accordance with the new minimum contamination test order so that minimal contamination occurs.

3. A method of controlling a reagent delivery system for delivering a plurality of different reagents into successive sample-containing reaction vessels in an automatic chemical analyzer for measurement of test specimens in a plurality corresponding of test items, comprising the steps of:

providing a reagent delivery device for delivering a plurality of different reagents corresponding to respective test items;

storing in memory means information representing a predetermined relationship between the test items with respect to the influence of contamination between said different reagents upon a measurement of said test specimens;

entering said information by entering means test items to be tested as successive samples;

storing in said memory means the entered test items to be tested as successive samples;

determining a minimum contamination test order for said entered test items in accordance with said stored information to minimize a number of occurrences of analytical measurement contamination between reagents of successive test items in said minimum contamination test order; and controlling the operation of said reagent delivery device whereby reagents, are successively delivered a minimum number of times by said reagent delivery device and wherein no washing of said reagent delivery device is performed between successive deliveries of reagents when the contamination test order determines a minimal number of contamination occurrences, and wherein washing of said reagent delivery device is performed only between successive deliveries of reagents if the contamination test order determines contamination between said reagents which affects said measurement.

* * * * *